US007013726B1

(12) United States Patent
Drummond et al.

(10) Patent No.: US 7,013,726 B1
(45) Date of Patent: Mar. 21, 2006

(54) FLUIDIC DEMAND APPARATUS AND MEMS FLOW SENSOR FOR USE THEREIN

(75) Inventors: Colin K. Drummond, Lakewood, OH (US); Joseph B. Richey, II, Chagrin Falls, OH (US)

(73) Assignee: Invacare Corporation, Elyria, OH (US)

( * ) Notice: Subject to any disclaimer, the term of this patent is extended or adjusted under 35 U.S.C. 154(b) by 0 days.

(21) Appl. No.: 10/994,512

(22) Filed: Nov. 22, 2004

(51) Int. Cl.
*G01F 15/00* (2006.01)
*F04B 17/00* (2006.01)

(52) U.S. Cl. .................................. 73/276; 417/413.2
(58) Field of Classification Search .................... None
See application file for complete search history.

(56) References Cited

U.S. PATENT DOCUMENTS

| | | | |
|---|---|---|---|
| 5,529,465 A * | 6/1996 | Zengerle et al. | 417/413.2 |
| 5,755,408 A | 5/1998 | Schmidt et al. | |
| 6,105,904 A | 8/2000 | Lisy et al. | |
| 6,354,839 B1 | 3/2002 | Schmidt et al. | |
| 6,743,021 B1 | 6/2004 | Prince et al. | |
| 6,752,152 B1 | 6/2004 | Gale et al. | |

OTHER PUBLICATIONS

GP-03X MEMS MicroValve, iACTIV Corporation, Version 1.2, Feb. 2003.

\* cited by examiner

*Primary Examiner*—Harshad Patel
(74) *Attorney, Agent, or Firm*—Calfee, Halter & Griswold LLP

(57) ABSTRACT

A microvalve sensor for sensing fluid flow therethrough and generating an electrical signal indicative thereof comprises: a housing connectable inline with a fluid passageway; a microvalve disposed in the housing to permit fluid to flow unidirectionally through the housing, the microvalve including: a substrate; an insulating layer disposed over the substrate, the substrate and insulating layer including an orifice to accommodate fluid flow through the housing; and a diaphragm element disposed over the insulating layer, the diaphragm element including: a solid center portion having an area sufficient to cover the orifice, and an outer portion surrounding the center portion having a plurality of apertures for passing fluid from the orifice through the housing, the outer portion being affixed to the insulating layer around a periphery thereof, the diaphragm element and substrate forming opposite plates of a capacitor having a capacitance which changes with fluid flow through the housing; and a circuit coupled across the opposite plates of the capacitor and powered by an electrical source for measuring the capacitance of the capacitor and generating an electrical signal indicative thereof.

20 Claims, 5 Drawing Sheets

FLUIDIC DEMAND APPARATUS AND MEMS FLOW SENSOR FOR USE THEREIN

BACKGROUND OF THE INVENTION

The present invention is related to fluidic demand apparatus, in general, and more particularly, to fluidic demand apparatus employing a microvalve or micro electro-mechanical system (MEMS) flow sensor, and the microvalve or MEMS flow sensor itself.

An example of a fluidic demand apparatus includes an Oxygen conserver which is shown by way of example in the fluidic schematic diagram of FIG. 1. An Oxygen conserver controls the flow of Oxygen gas from a source to a patient on demand, i.e. when a patient inhales. Referring to FIG. 1, in fluidic demand apparatus, the fluid, like Oxygen gas, for example, is generally provided from a high pressure source, such as a storage tank 10. From the tank 10, the fluid is usually regulated by a regulator 12. A pressure gauge 14 may be provided at the tank 10 as an indication of the fluid remaining in the tank 10. In the present example, the fluid in the tank 10 is at a pressure of 2,000 pounds per square inch (psi) and the regulator 12 reduces the pressure to approximately 40 psi.

The fluid may exit from the regulator 12 at a pressure of approximately 40 psi through two tubes or passageways 16 and 18. The tube 16 may be coupled to a delivery tank 40 which is coupled through a tube 22 to an input of a shuttle valve 24. A variable flow restrictor 25 may be disposed at the tube 16. An output of the shuttle valve 24 is coupled through a tube 26 to a passageway 28 leading to the patient. Within the valve 24 is a piston 30 which is movable from a bottom or closed position to a top or open position (see dashed lines). The tube 18 may be coupled to a tee connection 32 which may be coupled to the top of the valve 24 through a tube 34 and to a bottom of a diaphragm container 38 through a tube 36. Fixed fluid flow restrictors 40 and 42 may be disposed at the tubes 18 and 36, respectively. Another tube 44 may couple the bottom of container 38 to the atmosphere through a variable restrictor 46. Yet another tube 48 couples a top of container 38 to the patient's tube 28 through a check valve 50. A diaphragm 52 within container 38 may be in a spring loaded position (solid line) to close off a passage between tubes 36 and 44.

In operation, when the patient starts to inhale fluid through tube 28, fluid is conducted through the check valve 50 in tube 48 which creates a pressure differential across the diaphragm 52 in container 38. When the differential pressure overcomes the spring bias force, the diaphragm 52 is forced upwards (see dotted line position) which permits fluid to flow from the regulator 12 through tubes 18 and 36, through an open passageway in container 38 and through tube 44 exiting to the atmosphere. Thus, the fluidic pressure holding piston 30 in valve 24 in the closed position is relieved allowing piston 30 to rise to the open position (dotted line). In this position, fluid flows from the delivery tank 20 through tubes 22, 26 and 28 to the patient. The apparatus will remain in this state while the patient is inhaling.

When the patient stops inhaling, the spring bias force on diaphragm 52 forces it downward to block the fluid passageway between tubes 36 and 44. In this state, fluidic pressure builds up in tube 34 to force the piston 30 to the closed position (solid line), thereby closing off the fluid flow between tubes 22 and 26 and to the patient via tube 28. The foregoing described operation will repeat itself upon demand. In the present example, this demand results from commencement of inhalation of the patient. Note that the demand should be sufficient enough to overcome the spring bias of the diaphragm 52 in container 38. Otherwise, no fluid will flow to the demanding entity. The fluid flow in the present example is limited by the various restrictors in the tubes. In some apparatus, the valve 24, diaphragm container 38 and restrictors 40, 42 and 46 may be integrated in a common mechanical unit.

The foregoing described mechanical fluidic demand apparatus is adequate for controlled delivery of fluid to a demanding entity; however, it has a number of drawbacks. For example, such apparatus is comprised of many individual fluidic components which are complex and expensive to assemble. The overall manufacture of such apparatus generally involves special tooling, and set-up and quality assurance procedures. In addition, the mechanical fluidic apparatus is difficult to service in the field leading to reliability and cost issues. Generally, field service of the apparatus involves replacement of parts. Also, from a clinical perspective, the response to patient inhalation is not considered sensitive enough for triggering fluid flow, i.e. the patient has to draw harder.

The present invention overcomes these drawbacks of the current fluidic demand apparatus by replacing the mechanically active parts with miniature, low power electrically operative units as will become more evident from the detailed description of the invention found herein below.

SUMMARY OF THE INVENTION

In accordance with one aspect of the present invention, a microvalve sensor for sensing fluid flow therethrough and generating an electrical signal indicative thereof comprises: a housing connectable inline with a fluid passageway; a microvalve disposed in the housing to permit fluid to flow unidirectionally through the housing, the microvalve including: a substrate; an insulating layer disposed over the substrate, the substrate and insulating layer including an orifice to accommodate fluid flow through the housing; and a diaphragm element disposed over the insulating layer, the diaphragm element including: a solid center portion having an area sufficient to cover the orifice, and an outer portion surrounding the center portion having a plurality of apertures for passing fluid from the orifice through the housing, the outer portion being affixed to the insulating layer around a periphery thereof, the diaphragm element and substrate forming opposite plates of a capacitor having a capacitance which changes with fluid flow through the housing; and a circuit coupled across the opposite plates of the capacitor and powered by an electrical source for measuring the capacitance of the capacitor and generating an electrical signal indicative thereof.

In accordance with another aspect of the present invention, fluidic demand apparatus for conducting fluid from a fluid source under pressure to a demanding entity comprises: an electrically operative fluidic valve connectable between the fluid source and demanding entity; and a fluid flow sensor connectable in a fluid passageway to the demanding entity, the sensor including a microvalve operative electrically to sense fluid flow demand from the demanding entity through the passageway and to generate an electrical signal to drive the fluidic valve in response thereto.

DETAILED DESCRIPTION OF THE INVENTION

Figure 1:
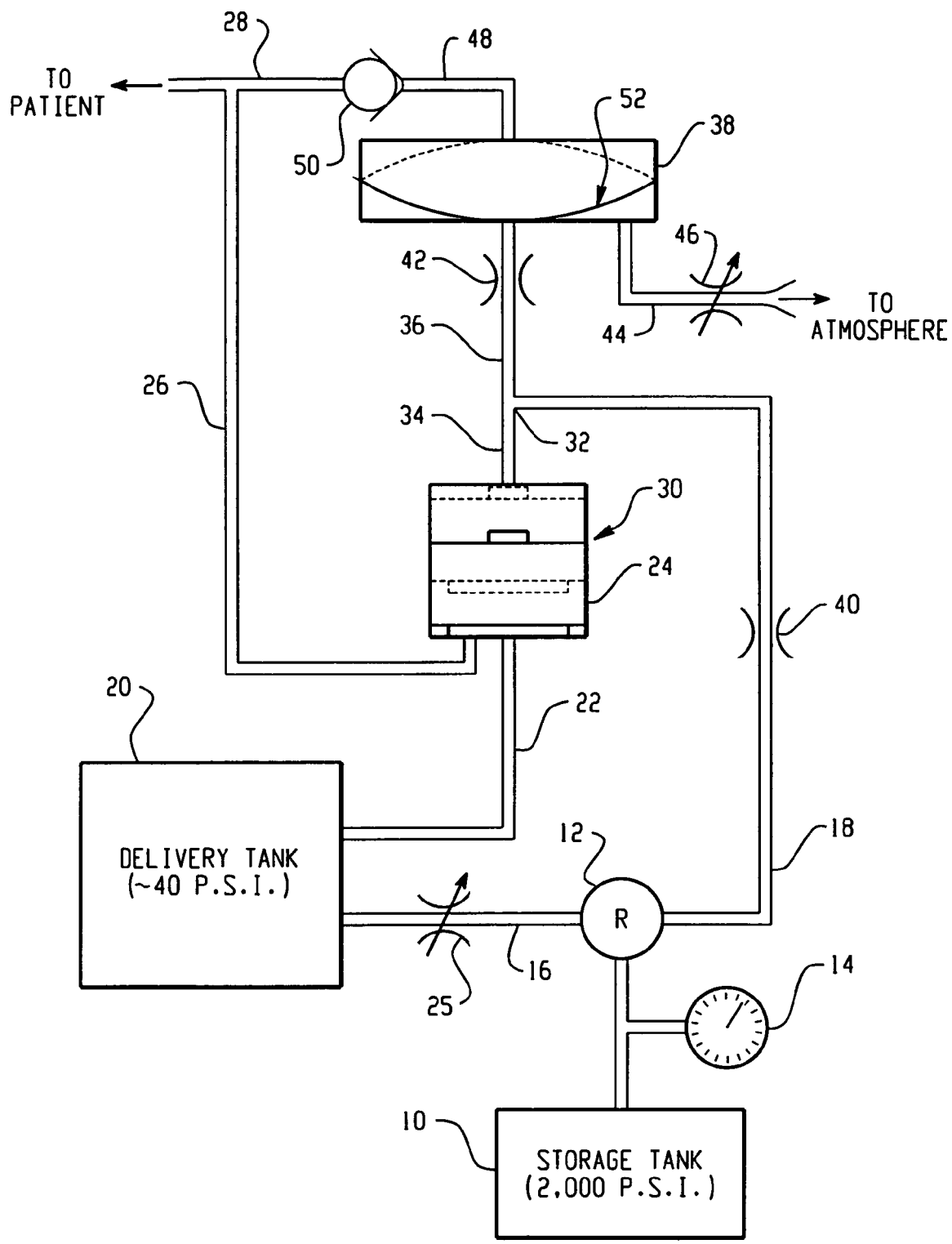
FIG. 1 is a fluidic schematic diagram of exemplary fluidic demand apparatus, like an Oxygen conserver, for example.
Figure 2:
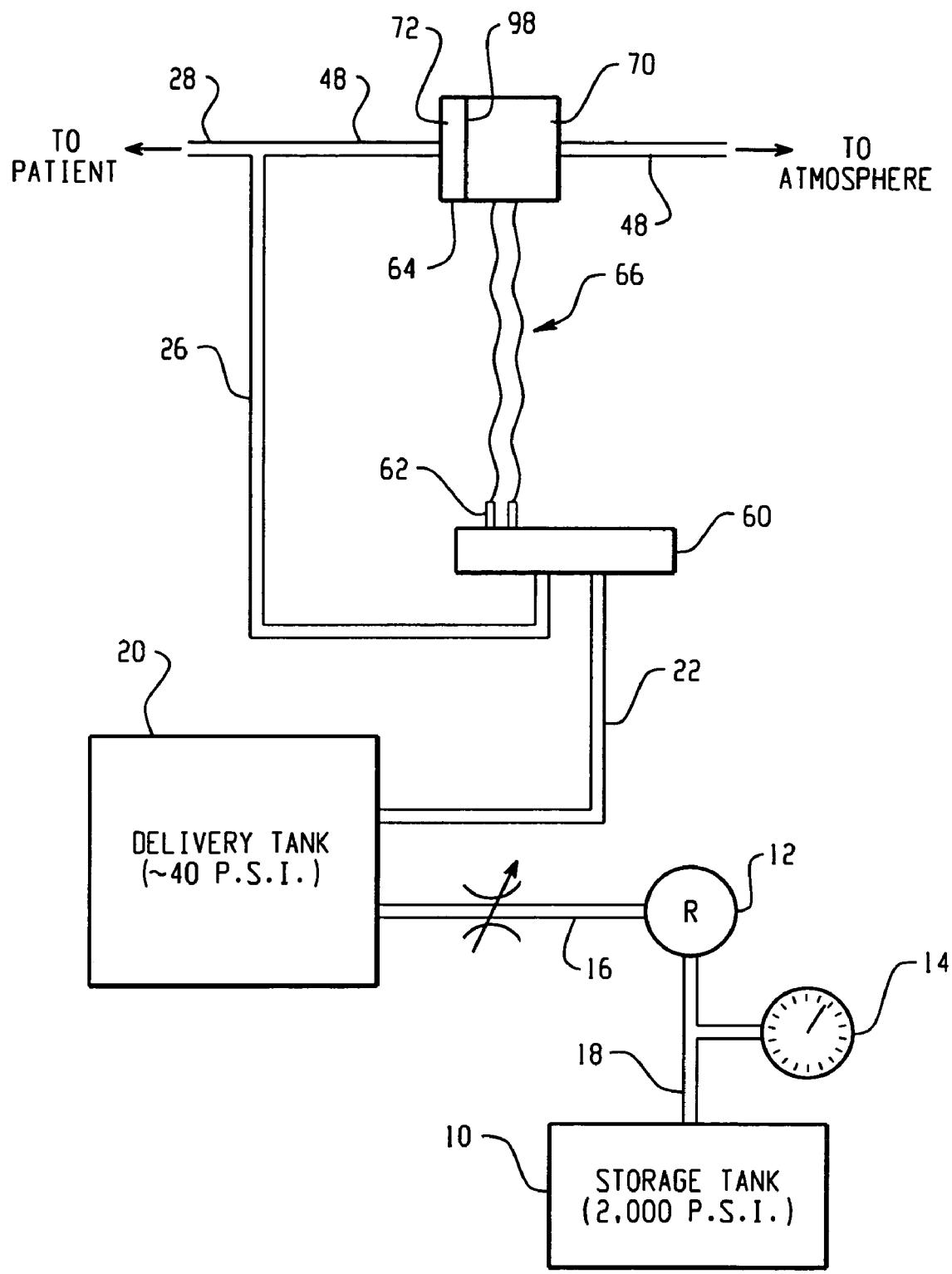
FIG. 2 is a block diagram schematic of fluidic demand apparatus suitable for embodying one aspect of the present invention.

FIG. 2 is a block diagram schematic of fluidic demand apparatus suitable for embodying one aspect of the present invention. Many of the components of the embodiment of FIG. 2 remain the same as described in connection with the embodiment of FIG. 1 and thus, will maintain their same functions and reference numbers. In the present embodiment, an electrically operated, fluidic valve 60 has its input and output fluidic ports coupled to tubes 22 and 26, respectively, and is driven by a voltage across electrical pins 62 to conduct fluid from tube 22 to tube 26. The fluidic valve 60 may be of the type manufactured by The Lee Company under model no. LHLXO500300B, for example. In addition, a flow rate sensor 64 is disposed at tube 48 between tube 28 and atmosphere, and employs a MEMS microvalve in its operation which will become more evident from the more detailed description found herein below. The sensor 64 is operative to perform the functions of check valve operation, differential pressure operational valve setting adaptable to the demanding entity, and flow rate sensing. The sensor 64 is operative to produce an electrical signal over signal lines 66 which are coupled to electrical pins 62 of the fluidic valve 60.

In operation, the patient or demanding entity will initially draw fluid from the atmosphere through tubes 28 and 48 and sensor 64. Note that the unchecked flow direction of the sensor 64 is from the atmosphere to the demanding entity or patient. When the sensor 64 senses fluid flow through the MEMS microvalve therein indicative of fluid demand, it produces the electrical signal over lines 66 at a level sufficient to drive the fluidic valve 60 open to deliver fluid from the delivery tank 20 to the demanding entity or patient through tubes 22, 26 and 28. In this state, the sensor 64 checks delivery of fluid to the atmosphere via lines 26 and 48. The fluidic valve 60 may be latched in the open position until the flow demand ceases. The foregoing described operation will continue for each flow demand cycle.

Figure 3:
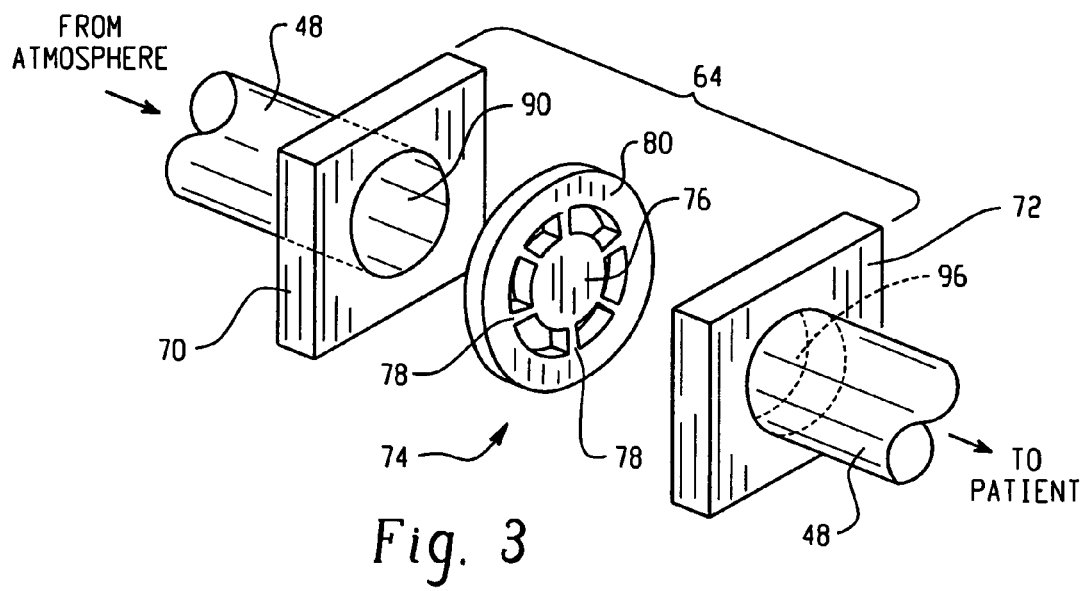
FIG. 3 is a break-away sketch of a microvalve fluid flow sensor suitable for embodying another aspect of the present invention.

FIG. 3 is a break-away sketch of sensor 64 shown coupled to tube 48. Referring to FIG. 3, sensor 64 may include two housings or compartments 70 and 72 for containing a MEMS microvalve 74 which may be of the type marketed by iACTIV Corporation under the model no. GP-03x, for example. In the present embodiment, the microvalve 74 is fabricated using MEMS micromaching techniques in a spooked wheel design comprising a center hub 76, a plurality of radial spokes 78 which extend from the hub 76 to an outer annular surface area 80. The overall diameter of the microvalve may be approximately 250 micrometers ($\mu$m), for example. The center hub 76 may have a diameter of approximately 150 $\mu$m and each of the radial spokes 78 may be about 20 $\mu$m in width. The center hub 76 and spokes 78 may be approximately 5 $\mu$m thick. The spokes 78 are spaced about the periphery of the hub 76 to permit passage of fluid through the open spaces therebetween as will become more evident from the following description.

Figure 4:
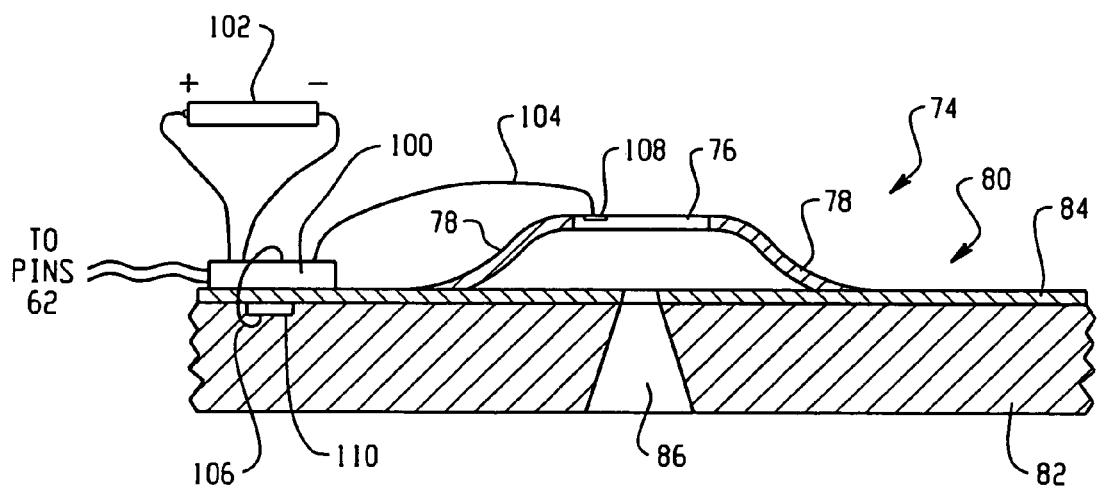
FIG. 4 is a cross-sectional, cut-away sketch of an exemplary microvalve suitable for use in the fluid flow sensor embodiment of FIG. 3.

FIG. 4 is a cross-sectional, cut-away sketch of an exemplary microvalve 74. Referring to FIG. 4, the microvalve 74 includes a disc shaped, rigid substrate 82 which may be fabricated from a silicon wafer. The thickness of the substrate 82 is commensurate with the thickness of the fabricating wafer which may vary between 50–100 $\mu$m, for example, from wafer to wafer. Disposed over the substrate 82 is an electrically insulating layer 84 which may be silicon nitride, for example, at a thickness of approximately a few $\mu$m, for example. A tapered orifice 86 may be micromachined through the substrate 82 and insulating layer 84 to permit fluid to flow therethrough. The diameter of the orifice 86 may be around 60–80 $\mu$m at its smallest opening.

The hub 76 and spokes 78 may be micromachined from a polysilicon layer over the insulating layer 84 with the hub 76 centered about the orifice 86 and the spokes 78 attached at one end to the hub 76 and at the other end to layer 84. Note that only one end of each of the spokes 78 is attached to the layer 84. The thickness of the polysilicon spokes 78 are such to provide an elastic stretching thereof to permit the hub 76 to extend above the layer 80 (as shown) so that fluid may flow through the orifice 86 and the openings between the spokes 78. In this manner, the hub 76 and spokes 78 act as a diaphragm with openings for fluid to flow through.

Figure 5A:
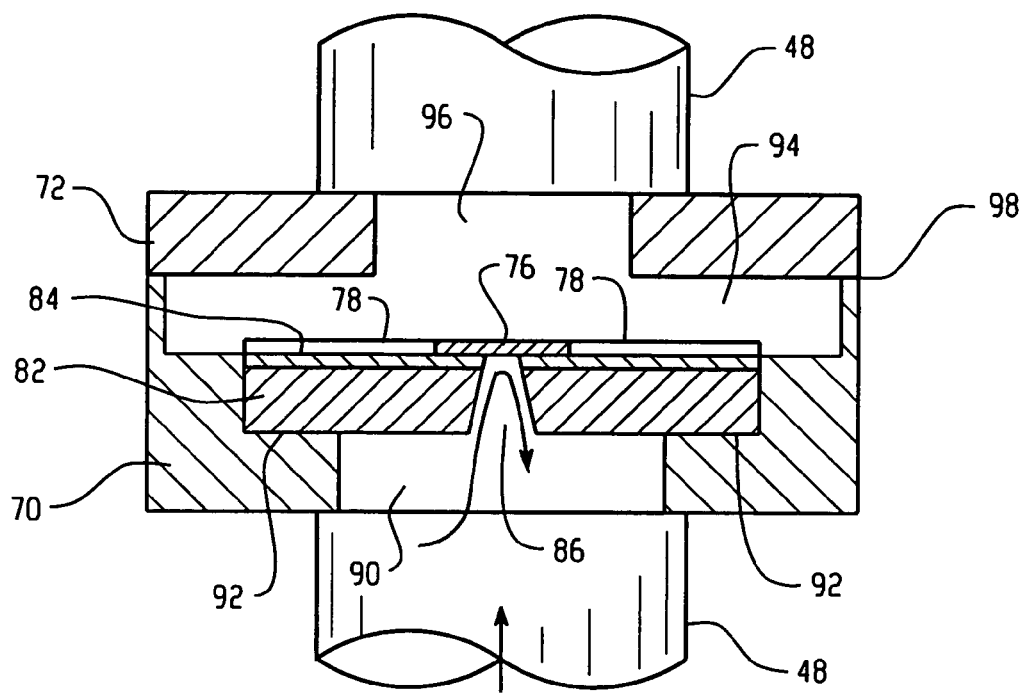
FIGS. 5A and 5B are cross-sectional sketches of operational states of the fluid flow sensor embodiment of FIG. 3.
Figure 5B:
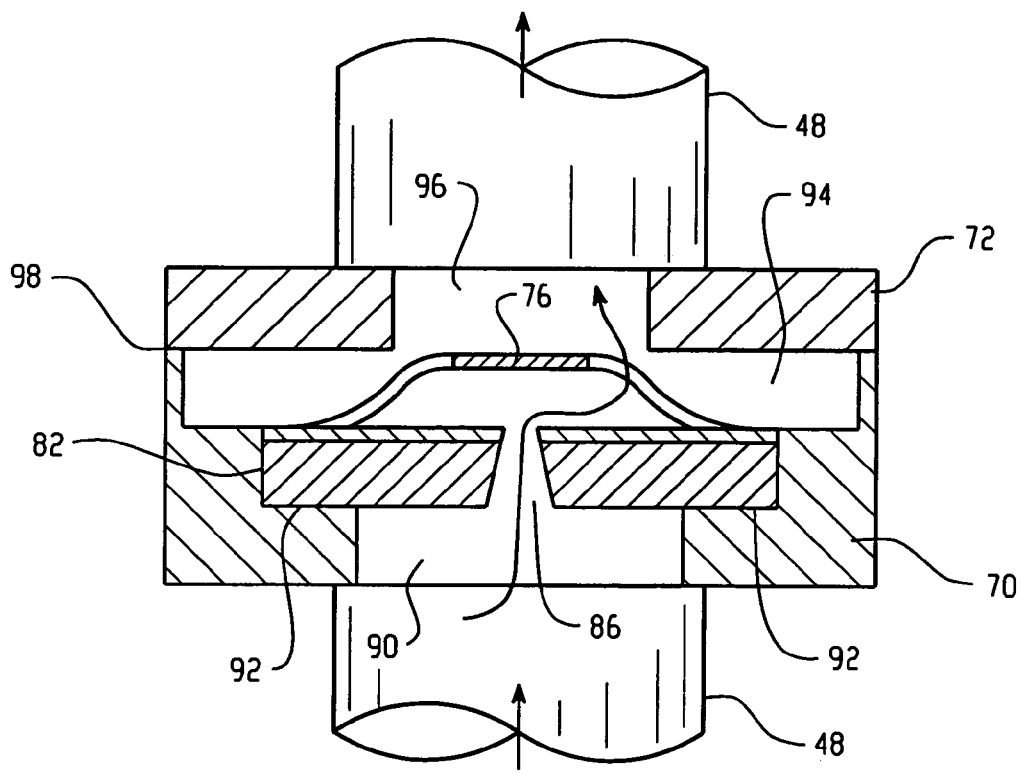

FIGS. 5A and 5B are cross-sectional sketches exemplifying operational states of the sensor 64. The unchecked flow direction is shown by the arrowed line in the FIGS. 5A and 5B. Referring to FIGS. 5A and 5B, the housing 70 includes an opening 90 through which one section of tube 48 may be attached. Around the circumference of opening 90 in housing 70 is an annular indented area 92 on which to seat and attach the substrate 82 of microvalve 74 in a permanent position. Housing 70 further includes a cavity 94 above the microvalve 74 and large enough to permit the hub 76 to extend upwards to an open position (see FIG. 5B). The height of the hub 76 in the open position may be approximately 20 $\mu$m above the orifice 86. Housing 72 also includes an opening 96 through which the other section of tube 48 may be attached. Housings 70 and 72 may be attached together and sealed around a seam 98 to encase the microvalve 74 therein.

In a no flow demand state, the hub 76 of microvalve 74 is seated on layer 84 over the orifice 86 as shown in FIG. 5A. In the present embodiment, the hub 76 may be held against the layer 84 with an adjustable electrostatic bias force. Referring back to FIG. 4, an integrated circuit 100 may be fabricated on the surface of layer 84, for example, and powered by an electrical source 102 which may be a miniature Lithium battery, for example. The circuit 100 may include an inverter circuit (not shown) to amplify the voltage potential of the battery source 102 to higher output voltage potentials. Output leads 104 and 106 from the inverter circuit of circuit 100 may be connected across the hub 76 and substrate 82 with opposite positive and negative polarities to impose the output voltage potential thereacross and create an attractive electrostatic force to maintain the hub against the layer 84, thus sealing off flow through the orifice 86.

In the example as shown in FIG. 4, lead 104 may be connected to a bonding pad 108 fabricated into the hub 76 and lead 106 may be connected to a bonding pad 110 fabricated into the substrate 82. Accordingly, the bias force or bias differential pressure to be overcome by the demand may be set by adjusting the voltage potential applied across the hub 76 and substrate 82. Note that fluid may not flow through the microvalve 74 in the checked direction, i.e. opposite the arrowed line, because the differential pressure in the checked direction will add to the electrostatic force to maintain the hub 76 against the layer 84 and seal off the orifice 86 as shown in FIG. 5A.

Figure 6:
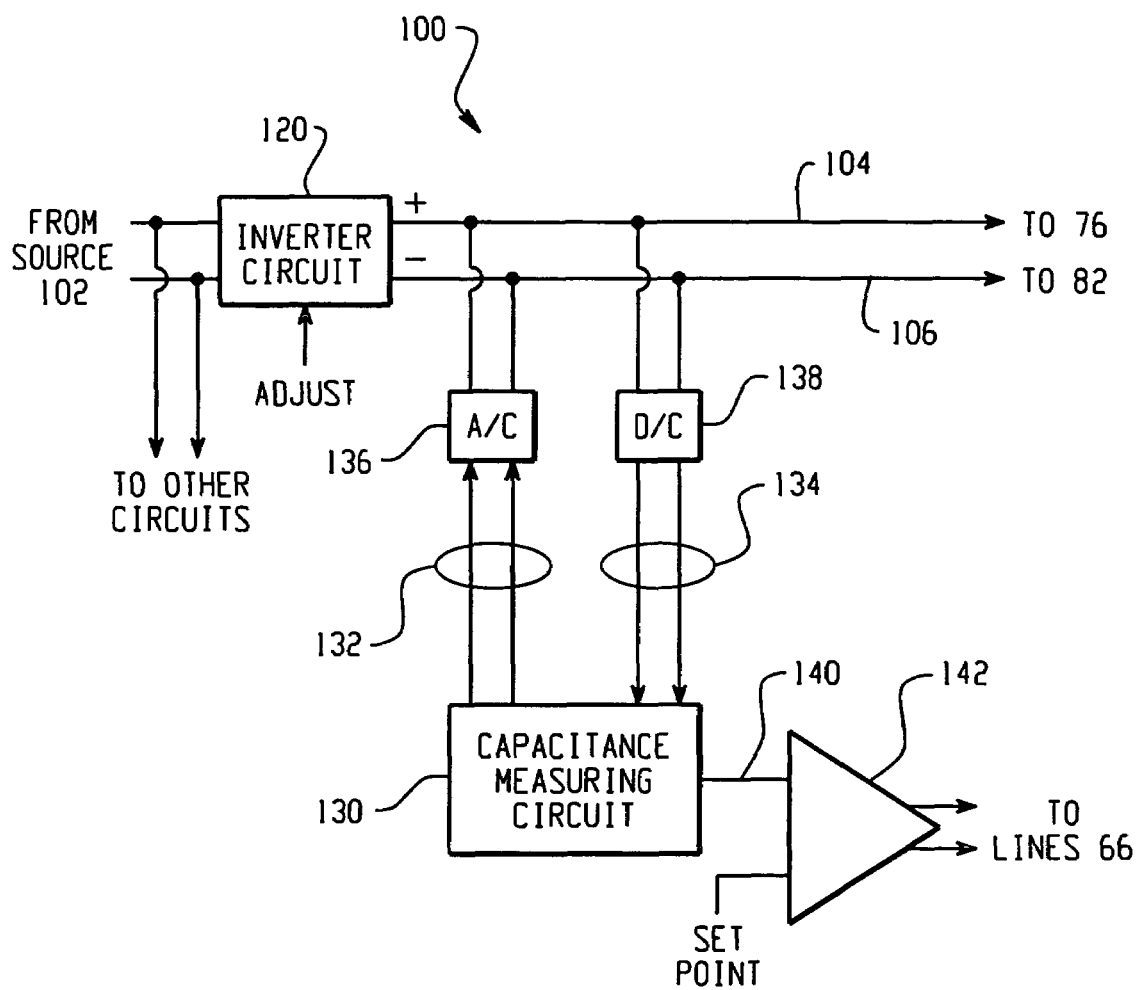
FIG. 6 is a block diagram schematic of an exemplary circuit embodiment suitable for use in the fluid flow sensor embodiment of FIG. 3.

A block diagram schematic of an exemplary integrated circuit 100 suitable for use in the embodiment of FIG. 4 is shown in FIG. 6. Referring to FIG. 6, as noted above, an inverter circuit 120 may be included in integrated circuit 100 to boost the DC voltage of the source 102 which may be around 1.5 volts to a higher electrostatic DC voltage applied across the diaphragm 76/78 and substrate 82 via leads 104 and 106, respectively. In the present embodiment, the electrostatic voltage may be adjustable through the inverter circuit 120 depending on the demand application and may vary from 20 volts DC to 80 volts DC, for example.

Once the bias electrostatic force on hub 76 is overcome by the demand, e.g. patient inhalation, the differential pressure across hub 76 will force it away from the orifice 86 as shown in the sketch of FIG. 5B. In this state, fluid may flow in the unchecked direction through the orifice 86 and openings between the spokes 78. Thus, in the present example, fluid may be drawn from the atmosphere through tube 48 as an indication of fluid demand or commencement of inhalation from the patient. The sensor 74 also includes circuitry to sense this flow rate and generate a voltage signal over lines 66 to drive the fluidic valve 60 (see FIG. 2).

It is recognized that the substrate 82 and diaphragm, comprising hub 76 and spokes 78, of the microvalve 74 form two plates of a capacitor. The distance between these two plates, i.e. substrate 82 and diaphragm 76/78, is held constant by the insulating (dielectric) layer 84 when the hub 76 is maintained against the orifice 86 (see FIG. 5A), but changes as the hub 76 moves away from the orifice 86 during fluid flow (see FIG. 5B). During fluid flow, the dielectric of the capacitor also changes to include both the insulating layer 84 and the fluid itself. Thus, the capacitance formed by the substrate 82 and diaphragm 76/78 changes between the no flow and flow states and is commensurate with the flow rate. A measure of this capacitance will provide an indication of fluid flow through the microvalve 74 in the present embodiment.

Referring back to FIG. 6, a capacitance measuring circuit 130 may be included in the integrated circuit 100 for measuring the capacitance between the plates 82 and 76/78. The circuit 130 may employ any of the well-known techniques for measuring capacitance comprising determining a resonance frequency of a tank circuit including the varying capacitance or determining time transient behavior of the varying capacitance in the time domain, for example. These techniques generally involve applying a stimulus signal over signal lines 132 across the capacitor and measuring a response signal from the capacitor over signal lines 134. Since in the present embodiment, the capacitor plates are at a DC voltage higher than the operating voltage of the circuit 130 which may be powered by the source 102, for example, the stimulus signal 132 may be A/C coupled to leads 104 and 106 through a coupler circuit 136 and the response signal 134 may be decoupled from the DC voltage of leads 104 and 106 by a decoupling circuit 138. Thus, the coupling circuits 136 and 138 permit the AC stimulus and response signals to modulate the quiescent electrostatic voltage signal of the leads 104 and 106.

In the present embodiment, the capacitance measuring circuit 130 determines the capacitance from the response signal 134 and produces therefrom a signal over line 140 indicative of the flow rate through the sensor 74. The flow rate signal 140 may be applied to one input of an amplifier circuit 142 to be compared with a set point signal that may be applied to another input of amplifier 142. The set point signal is adjustable according to the demand application to be commensurate with the minimum fluid flow rate through the sensor 74 for commencement of demand. Accordingly, when the signal 140 exceeds the set point signal, amplifier 142 generates a signal over lines 66 sufficient to drive the latching valve 60 to the open state whereupon fluid is delivered to the demanding entity (e.g. patient) via lines 22, 26 and 28 (see FIG. 2). Note that the microvalve 74 in sensor 64 will check fluid flow from dumping to the atmosphere through tube 48. When the demand is reduced below the minimum flow to keep valve 60 latched, it will close and cease delivery of fluid. The foregoing described cycle will be repeated for each new demand.

While the present invention has been described herein above in connection with one or more embodiments, it is understood that such embodiments were presented by way of example and not intended to limit the invention in any way. Accordingly, the present invention should not be limited to any specific embodiment, but rather construed in breadth and broad scope in accordance with the recitation of the claims appended hereto.

What is claimed is:

1. A microvalve sensor for sensing fluid flow therethrough and generating an electrical signal indicative thereof, said sensor comprising:

a housing connectable inline with a fluid passageway;

a microvalve disposed in said housing to permit fluid to flow unidirectionally through said housing, said microvalve including:

a substrate;

an insulating layer disposed over said substrate, said substrate and insulating layer including an orifice to accommodate fluid flow through said housing; and a diaphragm element disposed over said insulating layer, said diaphragm element including: a solid center portion having an area sufficient to cover the orifice, and an outer portion surrounding the center portion having a plurality of apertures for passing fluid from said orifice through said housing, said outer portion being affixed to said insulating layer around a periphery thereof, said diaphragm element and substrate forming opposite plates of a capacitor having a capacitance which changes with fluid flow through said housing; and a circuit coupled across the opposite plates of said capacitor and powered by an electrical source for measuring the capacitance of said capacitor and generating an electrical signal indicative thereof.

2. The sensor of claim 1 wherein the circuit includes a second circuit coupled to the substrate and diaphragm element for generating an electrostatic attractive voltage thereacross to create a bias force on the center portion of the diaphragm element over the orifice which prevents fluid from flowing therethrough until such bias force is overcome.

3. The sensor of claim 2 wherein the electrostatic attractive voltage generated by the second circuit is adjustable to create a desired bias force.

4. The sensor of claim 2 wherein the second circuit comprises an inverter circuit for amplifying the voltage of the electrical source to generate the electrostatic attractive voltage.

5. The sensor of claim 1 wherein the circuit is disposed in the housing.

6. The sensor of claim 1 wherein the circuit comprises an integrated circuit fabricated at the microvalve.

7. The sensor of claim 1 wherein the electrical source comprises a battery.

8. The sensor of claim 1 wherein the diaphragm element comprises a center hub portion and spokes extending radially from said hub portion to the insulating layer, the areas between the spokes forming the apertures of the diaphragm element.

9. The sensor of claim 8 wherein the diaphragm is micro-machined from a layer of polysilicon disposed over the insulating layer.

10. The sensor of claim 1 wherein the circuit is operative to generate the electrical signal when the measured capacitance exceeds a desired threshold.

11. Fluidic demand apparatus for conducting fluid from a fluid source under pressure to a demanding entity, said apparatus comprising:
    an electrically operative fluidic valve connectable between said fluid source and demanding entity; and
    a fluid flow sensor connectable in a fluid passageway to said demanding entity, said sensor including a microvalve operative electrically to sense fluid flow demand from said demanding entity through said passageway and to generate an electrical signal to drive said fluidic valve in response thereto.

12. The apparatus of claim 11 wherein the fluidic valve is operative in response to the electrical signal to conduct fluid from the fluid source to the demanding entity.

13. The apparatus of claim 12 wherein the fluidic valve is operative in response to the electrical signal to latch in the conductive state until fluid demand from the demanding entity ceases.

14. The apparatus of claim 11 wherein the fluid flow sensor comprises:
    a housing connectable inline with a fluid passageway;
    a microvalve disposed in said housing to permit fluid to flow unidirectionally through said housing, said microvalve including:
        a substrate;
        an insulating layer disposed over said substrate, said substrate and insulating layer including an orifice to accommodate fluid flow through said housing; and
        a diaphragm element disposed over said insulating layer, said diaphragm element including: a solid center portion having an area sufficient to cover the orifice, and an outer portion surrounding the center portion having a plurality of apertures for passing fluid from said orifice through said housing, said outer portion being affixed to said insulating layer around a periphery thereof, said diaphragm element and substrate forming opposite plates of a capacitor having a capacitance which changes with fluid flow through said housing; and
    a circuit coupled across the opposite plates of said capacitor and powered by an electrical source for measuring the capacitance of said capacitor and generating the electrical signal when said measured capacitance is indicative of a desired fluid flow through said housing.

15. The apparatus of claim 14 wherein the circuit includes a second circuit coupled to the substrate and diaphragm element for generating an electrostatic attractive voltage thereacross to create a bias force on the center portion of the diaphragm element over the orifice which prevents fluid from flowing therethrough until the fluid flow demand overcomes said bias force.

16. The apparatus of claim 15 wherein the electrostatic attractive voltage generated by the second circuit is adjustable to create a desired bias force.

17. The apparatus of claim 14 wherein the circuit is disposed in the housing.

18. The apparatus of claim 14 wherein the circuit comprises an integrated circuit fabricated at the microvalve.

19. The apparatus of claim 14 wherein the electrical source comprises a battery.

20. The apparatus of claim 14 wherein the circuit is operative to generate the electrical signal when the measured capacitance exceeds a desired threshold.

* * * * *